United States Patent [19]

Duhamel et al.

[11] Patent Number: 4,900,858

[45] Date of Patent: Feb. 13, 1990

[54] PROCESS FOR THE PREPARATION OF A 6-HALO-3-METHYL-1-TRIALKYL-SILYLOXY-1,3,5-HEXATRIENE

[75] Inventors: Lucette Duhamel; Pierre Duhamel, both of Mont-Saint Aignan; Jean-Pierre Lecouve, Caluire, all of France

[73] Assignee: Rhone-Poulenc Sante, Courbevoie, France

[21] Appl. No.: 265,342

[22] Filed: Oct. 27, 1988

Related U.S. Application Data

[63] Continuation of Ser. No. 24,524, Mar. 11, 1987, abandoned.

[30] Foreign Application Priority Data

Mar. 14, 1986 [FR] France .................................. 86 03669

[51] Int. Cl.$^4$ ............................................... C07F 7/18
[52] U.S. Cl. ..................................................... 556/470
[58] Field of Search ........................................ 556/470

[56] References Cited

U.S. PATENT DOCUMENTS 3,472,888 10/1969 Bazouin ............................... 556/470

FOREIGN PATENT DOCUMENTS 3020446 12/1980 Fed. Rep. of Germany ...... 556/470
2503166 3/1981 France ................................ 556/470

OTHER PUBLICATIONS

House et al., "J. of Org. Chem.", 34, No. 8 (1969), pp. 2324–2336.
The Journal of Organic Chemistry, vol. 34, No. 8, 1969, pp. 2324–2336; H. O. House et al., "The Chemistry of Carbanions, XVIII".

Primary Examiner—Paul F. Shaver
Attorney, Agent, or Firm—Stevens, Davis, Miller & Mosher

[57] ABSTRACT

6-halo-3-methyl-1-trialkylsilyloxy-1,3,5-hexatriene, useful as an intermediate in the preparation of terpene compounds, is prepared by reaction of a 6-halohexadienal with a halo-silane in the presence of a tertiary amine.

3 Claims, No Drawings

PROCESS FOR THE PREPARATION OF A 6-HALO-3-METHYL-1-TRIALKYLSILYLOXY-1,3,5-HEXATRIENE

This application is a continuation of application Ser. No. 024,524, filed Mar. 11, 1987.

The present invention relates to the preparation of 6-halo-3-methyl-1-trialkylsilyloxy-1,3,5-hexatrienes of the general formula:

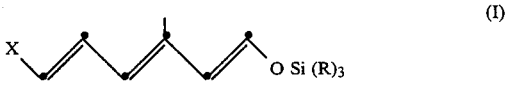
(I)

in which X denotes a halogen atom, preferably a bromine atom, and R denotes an alkyl radical containing 1 to 4 carbon atoms.

The products of general formula (I) are particularly useful in terpene synthesis, e.g. for the preparation of retinal from β-ionone. More particularly, after conversion into metal derivatives by halogen-metal exchange, they can react with carbonyl compounds (in particular aldehydes and ketones) under the conditions described in French Patent FR 81/06,500 (2,503,166).

French Patent FR 81/06,500 (2,503,166) describes the preparation of 2-bromo-1-trimethylsilyloxyethylene by the action of bromine on the corresponding trialkylsilyl enol ether followed by dehydrohalogenation by the action of a tertiary amine. However, this process does not always yield satisfactory results when higher homologues are prepared.

It has now been found, and this forms the subject of the present invention, that the products of general formula (I) may be obtained, in good yields, by the reaction of at least one molecular equivalent of a halosilane (e.g. bromotrimethylsilane), in the presence of at least 1.2 equivalents of a tertiary amine (e.g. triethylamine) with a 6-halo-3-methylhexadienal, the operation being carried out in an inert organic solvent such as an aliphatic hydrocarbon (e.g. pentane) or a nitrile (e.g. acetonitrile), or a mixture of these solvents, at a temperature of −10° to +30° C.

A 6-halo-3-methylhexadienal, such as a 6-halo-3-methyl-3,5-hexadienal, used as starting material, may be obtained by hydrolysis of a compound of the formula:

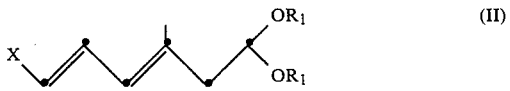
(II)

in which X denotes a halogen atom and $R_1$ denotes an alkyl radical containing 1 to 4 carbon atoms, with an inorganic acid (e.g. hydrobromic acid) in an aqueous organic medium (e.g. acetone-water).

The compounds of formula (II) may be obtained by the action of a halomethylphosphonium halide, such as bromoethyltriphenylphosphonium bromide, on a 5,5-dialkoxy-3-methyl-2-pentenal, the operation being carried out in the presence of an alkali metal alcoholate, such as potassium tert-butylate, in an anhydrous organic solvent, such as tetrahydrofuran, at a temperature of between −70° and 0° C.

The 5,5-dialkoxy-3-methyl-2-pentenal may be prepared by the process described in French Patent FR 77/15,070 (2,391,181).

The following Examples illustrate the invention.

EXAMPLE 1

6-Bromo-3-methyl-3,5-hexadienal (0.95 g; 5 mmol) dissolved in acetonitrile (25 cc) and pentane (25 cc) is introduced, under an argon atmosphere, into a 100-cc round flask fitted with a septum and a magnetic stirrer. Triethylamine (1 g; 10 mmol, i.e. 2 equivalents) is then added. After the mixture has been cooled to 0° C., bromotrimethylsilane (1.53 g; 2 equivalents) is added dropwise. The temperature is allowed to return to about 20° C. After 48 hours the reaction is complete. The acetonitrile phase is extracted with pentane (4×15 cc) under an argon atmosphere. After evaporation of the solvent and distillation, 6-bromo-3-methyl-1-trimethylsilyloxy-1,3,5-hexatriene (0.53 g) is obtained (b.p. 0.06 kPa=92°-95° C.). The yield is 46.8%. The structure of the product obtained is confirmed by the infrared spectrum and the proton nuclear magnetic resonance spectrum.

6-Bromo-3-methyl-3,5-hexadienal may be prepared as follows. 6-Bromo-3-methyl-1,1-dimethoxy-3,5-hexadiene (1.25 g; 5.31 mmol) dissolved in acetone (48 cc) is introduced, under an argon atmosphere, into a 250-cc three-necked round flask fitted with a condenser, a thermometer, a septum and a magnetic stirrer. Water (0.7 cc) is added, followed by Ionol (0.1 g). The mixture is refluxed for 1 minute. A solution (0.6 cc) of 48% aqueous hydrobromic acid (3 cc) in acetone (141 cc) is then added and the materials are refluxed for 40 minutes. The solution becomes brown.

After the mixture has been cooled to a temperature of about 20° C., pentane (50 cc) is added quickly, followed by a 5% aqueous solution of sodium bicarbonate (1 cc) and the mixture is stirred vigorously for 15 minutes. The organic phase is extracted with pentane (5×20 cc), and the extract is washed with water to neutrality (2×3 cc).

The combined organic phases are dried over sodium carbonate. After filtration and evaporation of the solvent, a crude product (0.85 g) is obtained, which contains 6-bromo-3-methyl-3,5-hexadienal (0.75 g) and Ionol (0.1 g). The yield is 75%. The structure of the product obtained is confirmed by the infrared spectrum and by the proton nuclear magnetic spectrum.

6-Bromo-3-methyl-1,1-dimethoxy-3,5-hexadiene may be prepared as follows. Bromomethyltriphenylphosphonium bromide (12.24 g; 32.8 mmol) suspended in anhydrous tetrahydrofuran (160 cc) is introduced, under an argon atmosphere, into a 500-cc three-necked round flask fitted with a magnetic stirrer and a thermometer. After the mixture has been cooled to −70° C., potassium tert-butylate (3.15 g; 32.8 mmol) is added in small portions over 10 minutes. The mixture is stirred for 1 hour 30 minutes at −70° C. The white suspension turns orange. 5,5-Dimethoxy-3-methyl-2-pentenal (3.3 g; 20.9 mmol, i.e. 0.75 equivalent) dissolved in tetrahydrofuran (17 cc) is then added over 10 minutes at −70° C. The reaction mixture is kept for 1 hour at 0° C. and then for 1 hour 30 minutes at a temperature of about 20° C. Water (85 cc) is added quickly and the mixture is then stirred vigorously for 10 minutes.

The reaction mixture is taken up with ether (100 cc). After phase separation the aqueous phase is extracted with ether (6×40 cc). The organic phases are dried over magnesium sulphate. After filtration and evaporation of the solvents, a viscous oil is obtained, to which sand (10 g) is added. After filtration through silica, and elution with pentane, 6-bromo-3-methyl-1,1-dimethoxy- 3,5-hexadiene (4.13 g) is obtained. The yield is 84%. The structure of the product obtained is confirmed by the infrared spectrum and the proton nuclear magnetic resonance spectrum.

EXAMPLE 2

6-Bromo-3-methyl-1-trimethylsilyloxy-1,3,5-hexatriene (0.44 g; 1.9 mmol) dissolved in anhydrous ether (12 cc) is introduced, under an argon atmosphere, into a 25-cc round flask fitted with a magnetic stirrer, a thermometer and a septum. After the mixture has been cooled to −70° C., tert-butyllithium (1.5 cc, 1.7N in pentane; 2.85 mmol, i.e. 1.5 equivalent) is added over 7 minutes. The mixture is left for 70 minutes at −70° C. β-Ionone (0.33 g; 1.71 mmol, i.e. 0.9 equivalent) dissolved in ether (4 cc) is then added at this temperature.

The reaction mixture is kept for 40 minutes at between −20° and −30° C. It is then cooled to −60° C. and N hydrochloric acid (5.7 cc) is added quickly. The reaction mixture is kept in a bath at 0° C. for 5 minutes and then at a temperature of about 20° C. for 30 minutes, with vigorous stirring. The golden-yellow reaction mixture is taken up with ether. After phase separation, the aqueous phase is extracted with ether. The combined organic phases are washed with water to neutrality and are then dried over sodium carbonate. After filtration and evaporation of the solvent, a crude product (0.58 g) is obtained which is purified by chromatography. After elution with a mixture of petroleum ether and ether (98.5/1.5 by volume), retinal (0.112 g) is obtained. The proportion of β-ionone converted is 37%. The yield is 23%, based on 6-bromo-3-methyl-1-trimethylsilyloxy-1,3,5-hexatriene, and 62% based on the reacted β-ionone.

We claim:

1. A process for the preparation of a 6-halo-3-methyl-1-trialkylsilyloxyhexatriene of the formula:

in which X denotes a halogen atom and R denotes an alkyl radical of 1 to 4 carbon atoms, which comprises reacting a halosilane of the formula:

with a 6-halo-3-methyl-hexadienal of formula:

in which X and R are as hereinbefore defined, in the presence of a tertiary amine and in an inert organic solvent at a temperature of −10° to +30° C.

2. Process according to claim 1, wherein bromotrimethylsilane is reacted with the 6-halo-3-methylhexadienal in the presence of triethylamine.

3. Process according to claim 1, wherein the 6-halo-3-methylhexadienal is 6-bromo-3-methyl-3,5-hexadienal.

* * * * *